US012557893B2

(12) United States Patent     (10) Patent No.:   US 12,557,893 B2
Li et al.     (45) Date of Patent:   Feb. 24, 2026

(54) NAIL DRILL FOR EASY CONTROL

(71) Applicant: SHENZHENSHI NANJIAKEJIXINXI YOUXIANGONGSI, Shenzhen (CN)

(72) Inventors: Jinfang Li, Shenzhen (CN); Xinlang Zhan, Shenzhen (CN)

(73) Assignee: SHENZHENSHI NANJIAKEJIXINXI YOUXIANGONGSI, Shenzhen (CN)

( * ) Notice: Subject to any disclaimer, the term of this patent is extended or adjusted under 35 U.S.C. 154(b) by 314 days.

(21) Appl. No.: 18/397,679

(22) Filed: Dec. 27, 2023

(65) Prior Publication Data

US 2025/0098836 A1     Mar. 27, 2025

(30) Foreign Application Priority Data

Sep. 25, 2023    (CN) ......................... 202322610281.X

(51) Int. Cl.
    *A45D 29/14*     (2006.01)
    *A45D 29/05*     (2006.01)
    *A61B 17/54*     (2006.01)

(52) U.S. Cl.
    CPC .............. *A45D 29/14* (2013.01); *A61B 17/54* (2013.01); *A45D 29/05* (2013.01)

(58) Field of Classification Search
    CPC ......... A45D 29/14; A45D 29/05; A61B 17/54
    See application file for complete search history.

(56) References Cited

U.S. PATENT DOCUMENTS 4,440,182 A * 4/1984 Holm ..................... A45D 29/14
                                       132/75.6
11,484,107 B2 * 11/2022 Hurter ................... G08C 17/02
(Continued)

FOREIGN PATENT DOCUMENTS

CN      114680442 A * 7/2022 ............. A45D 29/14
CN      114747858 A * 7/2022 ............. A45D 29/14
(Continued)

OTHER PUBLICATIONS

"MelodySusie Cordless Nail Drill, Professional 30000 RPM Rechargeable Electric Nail File for Acrylic and Gel Nails, Portable Efile Nail Machine Kit for Manicure Pedicure and Polishing-SP1," Aug. 10, 2023, https://www.amazon.com/MelodySusie-Cordless-Professional-Rechargeable-Polishing-SP1/dp/B0C9JG61H8?ref_=ast_sto_dp&th=1, retrieved Dec. 27, 2023, 4 pages.

(Continued)

*Primary Examiner* — Tatiana L Nobrega

(74) *Attorney, Agent, or Firm* — MUNCY, GEISSLER, OLDS & LOWE, P.C.

(57) ABSTRACT

The present disclosure discloses a nail drill for easy control, including a shell assembly, a polish head, a motor assembly, a speed regulating assembly, and a flexible top cover assembly. The speed regulating assembly regulates a rotational speed of the motor assembly and a start or stop of the motor assembly. The flexible top cover assembly is rotatably provided at one end of the shell assembly away from the polish head and covers the speed control assembly. Users can adjust the rotation speed of the motor assembly, the start or stop of the motor assembly by tilting the flexible top cover assembly to the desktop for sliding. Pressing a top of the flexible top cover assembly stops the motor assembly, pressing the top of the flexible top cover assembly again rotates the motor assembly, achieving a pause function of the motor assembly.

9 Claims, 3 Drawing Sheets

(56)                    References Cited

U.S. PATENT DOCUMENTS

| | | | |
|---|---|---|---|
| 12,239,099 B2 * | 3/2025 | Johnson ................ | A01K 13/00 |
| 2020/0154845 A1 * | 5/2020 | Feng ....................... | H01H 3/12 |
| 2021/0100332 A1 * | 4/2021 | Hsieh ...................... | A61L 2/26 |

FOREIGN PATENT DOCUMENTS

| | | | |
|---|---|---|---|
| CN | 220141022 U | * 12/2023 | |
| DE | 19518591 A1 | * 12/1996 | ............. H02P 7/285 |

OTHER PUBLICATIONS

MelodySusie, "SP1-Cordless & Stepless Speed Nail Drill 30000 RPM," Aug. 10, 2023, https://www.melodysusie.com/products/sp1-cordless-stepless-speed-rechargeable-nail-drill-30000-rpm, retrieved Dec. 27, 2023, 12 pages.
U.S. Appl. No. 29/877,402, filed Jun. 6, 2023.

* cited by examiner

NAIL DRILL FOR EASY CONTROL

CROSS-REFERENCES TO RELATED APPLICATIONS

This application claims priority to Chinese Patent Application No. 202322610281.X, filed on Sep. 25, 2023, the content of all of which is incorporated herein by reference.

TECHNICAL FIELD

The present disclosure relates to the technical field of nail dills, in particular to a nail drill for easy control.

BACKGROUND

In the process of nail art, nail drill is usually matched with different grinding needles, and is applied in the process of manicure, nail removal, styling, etc. Currently, a controlling method of a wireless nail drill on the market is pressing a button on the nail drill to adjust rotational speed (generally there are limited gears, commonly including three gears: slow, medium, and fast) and control the nail drill to start or stop, or relying on a knob of an additional controller to adjust rotational speed, start, and stop of a motor. Either way, it basically requires a user to operate with both hands of the user, which means that the user must hold the nail drill in one hand and control the nail drill with another hand at the same time, inconveniently and inefficiently.

Therefore, the prior art still needs to be improved and developed.

SUMMARY

In view of the above deficiencies of the prior art, the present disclosure aims to provide a nail drill for easy control to solve the problem of inconvenient speed adjustment and low working efficiency of the existing nail drills.

To solve the above problem, the disclosed technical scheme of the present disclosure is as follows:

A nail drill for easy control, including:
a shell assembly, where a mounting cavity is provided inside the shell assembly;
a motor assembly, provided inside the mounting cavity;
a polish head, provided at one end of the shell assembly, where the polish head is connected to an output end of the motor assembly;
a speed regulating assembly, provided at another end of the shell assembly, electrically connected to the motor assembly, where when the speed regulating assembly is rotated, a rotational speed of the motor assembly is adjusted, and when the speed regulating assembly is pressed, a start or a stop of the motor assembly is controlled; and
a flexible top cover assembly, rotatably provided at one end of the shell assembly away from the polish head, and the flexible top cover assembly covers the speed regulating assembly.

Optionally, the flexible top cover assembly includes a rotary sleeve and a flexible top cover, one end of the rotary sleeve is connected to one end of the shell assembly away from the polish head, and another end of the rotary sleeve is connected to the flexible top cover, and the flexible top cover covers the speed regulating assembly.

Optionally, the flexible top cover is provided with a connection portion at one end of the flexible top cover away from the shell assembly, the connection portion extends in a direction from the flexible top cover towards the speed regulating assembly, and the connection portion is connected to the speed regulating assembly.

Optionally, the flexible top cover is a silicone flexible top cover or a rubber flexible top cover.

Optionally, an annular groove is provided at an outer surface of the rotary sleeve, a ring protrusion is provided at an inner surface of the flexible top cover, and the ring protrusion is snapped into the annular groove.

Optionally, the shell assembly includes:
a shell, where one end of the shell is connected to the polish head, and another end of the shell is connected to the flexible top cover assembly;
a front shell, provided inside the shell;
a back shell, provided inside the shell, where the back shell and the front shell are enclosed to form the mounting cavity;
a fixing cylinder, sleeved at both one end of the front shell away from the polish head and one end of the back shell away from the polish head, for fixedly connecting the front shell and the back shell together; and
a fixing ring, sleeved at both one end of the front shell close to the polish head and one end of the back shell close to the polish head, for fixedly connecting the front shell and the back shell together.

Optionally, the front shell is provided with a first elastic protrusion at one end of the front shell away from the polish head, the back shell is provided with a second elastic protrusion at one end of the back shell away from the polish head, the first elastic protrusion and the second elastic protrusion respectively abuts against an inner wall of the fixing cylinder, and an outer wall of the fixing cylinder is rotatably connected with the rotary sleeve.

Optionally, the nail drill for easy control further includes a display, the display is provided at a side wall of the shell assembly, the display is electrically connected to the motor assembly for displaying a rotational speed of a motor.

Optionally, the nail drill for easy control further includes:
a battery, provided inside the mounting cavity, and electrically connected to the motor assembly for powering the motor assembly; and
a charging connector, provided inside the mounting cavity, where an output end of the charging connector is electrically connected to the battery, and an input end of the charging connector is provided on a side wall of the shell assembly for electrically connecting to an external power source.

Optionally, the nail drill for easy control further includes a power switch button, the power switch button is provided at the shell assembly, and the power switch button is electrically connected to the motor assembly for controlling a connection and a disconnection of a power supply.

In summary, the beneficial effects of the utility model are as follows.

The nail drill for easy control in the present disclosure includes a shell assembly, a polish head, a motor assembly, a speed regulating assembly, and a flexible top cover assembly. The speed regulating assembly regulates the rotational speed of the motor assembly and the start and stop of the motor assembly, and the flexible top cover assembly is rotatably provided at one end of the shell assembly away from the polish head and covers with the speed regulating assembly. When in use, the nail drill is held in the hand, and the flexible top cover assembly of the nail drill is tilted to the desktop and slid to adjust the rotational speed of the motor assembly, and the rotational speed is adjusted with one hand, which greatly frees the user's other hand and enables the user to adjust the rotational speed without having to additionally put down the work of the hand to adjust the rotational speed in the process of manicure. When a top of the flexible top cover assembly is pressed, the motor assembly stops, and the motor assembly is rotated by pressing the top of the flexible top cover assembly again, which achieves a pause function of the motor assembly. It can simplify the operation process of adjusting the rotation speed during manicure, and is easy to use.

BRIEF DESCRIPTION OF THE DRAWINGS

In order to more clearly illustrate the technical solutions in the embodiments of the present disclosure or the prior art, the accompanying drawings to be used in the embodiments or the prior art are briefly introduced below, and it is obvious that the accompanying drawings in the following description are only some embodiments documented in the present disclosure. For those ordinary skilled in the art, other drawings can be obtained according to these accompanying drawings without creative work.

Among them: 100, shell assembly; 110, front shell; 120, back shell; 130, fixing cylinder; 140, fixing ring; 150, shell; 200, polish head; 300, motor assembly; 310, rotary shaft hinge; 320, motor; 400, circuit board; 500, speed regulating assembly; 510, base; 520, rotary shaft; 600, flexible top cover assembly; 610, rotary sleeve; 620, flexible top cover; 621, connection portion; 622, ring protrusion; 623, connection hole; 700, battery; 800, power switch button.

DETAILED DESCRIPTION OF THE EMBODIMENTS

In order to enable those skilled in the art to better understand the technical solutions of the present disclosure, the technical solutions in the embodiments of the present disclosure are clearly and completely described below in combination with the accompanying drawings in the embodiments of the present disclosure, and it is obvious that the described embodiments are only a part of the embodiments of the present disclosure and not all of the embodiments. Based on the embodiments in the present disclosure, other embodiments obtained by those ordinary skilled in the art without creative work are within the protection scope of the present disclosure.

Figure 1:
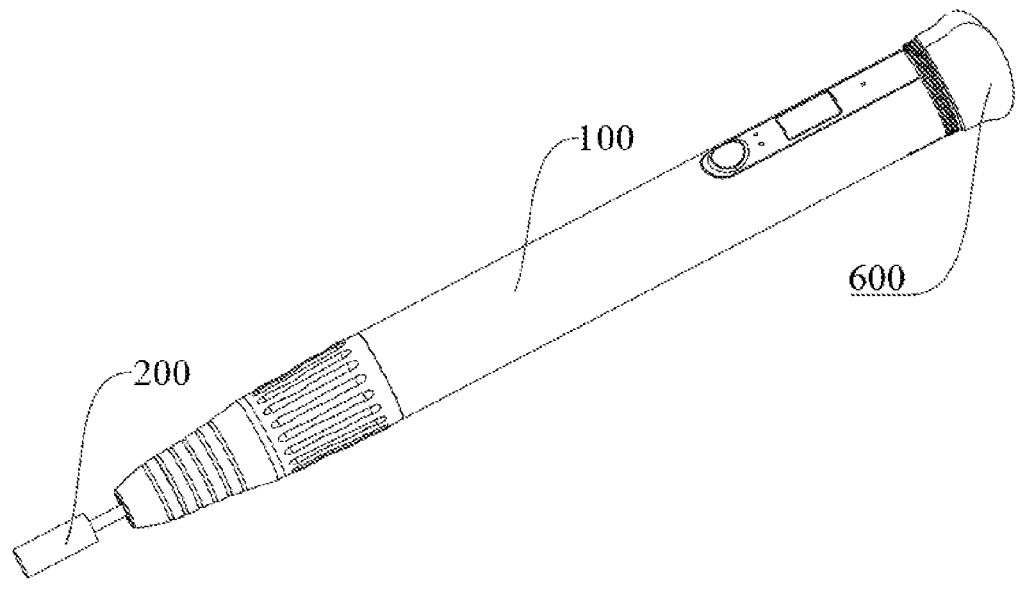
FIG. 1 is a schematic diagram of an exploded view of a nail drill for easy control in the present disclosure.
Figure 2:
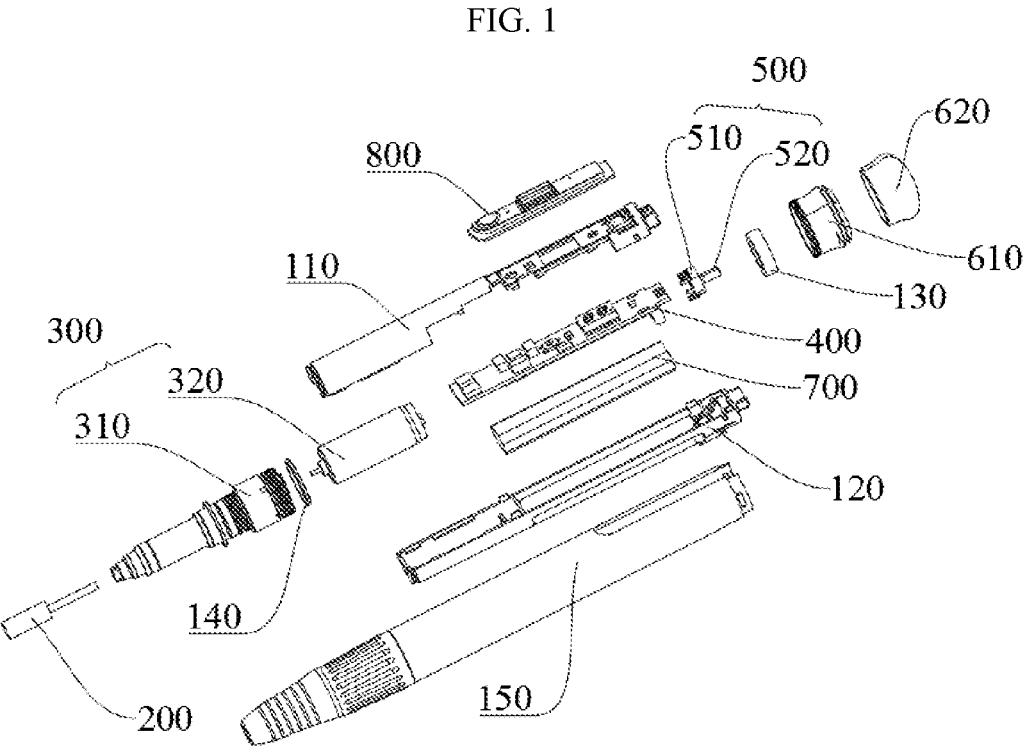
FIG. 2 is a schematic diagram of a partial sectional view of a nail drill for easy control in the present disclosure.

Referring to FIGS. 1 and 2, an embodiment of the present disclosure discloses a nail drill for easy control, the nail drill includes a shell assembly 100, a polish head 200, a motor assembly 300, a speed regulating assembly 500, and a flexible top cover assembly 600. The shell assembly 100 is provided with a mounting cavity inside the shell assembly 100, the motor assembly 300 is arranged inside the mounting cavity. The polish head 200 is arranged at one end of the shell assembly 100, and is connected to an output end of the motor assembly 300. The speed regulating assembly 500 is provided at another end of the shell assembly 100, and electrically connected to the motor assembly 300, the rotational speed of the motor assembly 300 can be adjusted when the speed regulating assembly 500 is rotated, and the start or stop of the motor assembly 300 can be controlled when the speed regulating assembly 500 is pressed. The flexible top cover assembly 600, is rotatably located at one end of the shell assembly 100 away from the polish head 200, and the flexible top cover assembly 600 is provided to cover the speed regulating assembly 500.

In this embodiment, the speed regulating assembly 500 includes a base 510 and a rotary shaft 520, the base 510 is electrically connected to the motor assembly 300, the rotary shaft 520 is movably connected to the base 510. By rotating the rotary shaft 520, the rotational speed of the motor assembly 300 can be adjusted, and by pressing on the rotary shaft 520, the start or stop of the motor assembly 300 can be controlled.

Specifically, when working, the shell assembly 100 is held in a hand, nails are polished through the polish head 200. When the speed needs to be adjusted, the flexible top cover assembly 600 is tilted on a tabletop for sliding, the flexible top cover assembly 600 rotates the rotary shaft 520, the rotary shaft 520 adjusts the speed of the motor assembly 300 through the base 510. When it is necessary to pause, a top of the flexible top cover assembly 600 is pressed and the rotary shaft 520 is pressed down, and the motor assembly 300 is controlled to stop through the base 510, and when the flexible top cover assembly 600 is pressed down again, the rotary shaft 520 is pressed down, and the motor assembly 300 is controlled to start through the base 510.

In this embodiment, by rotating the flexible top cover assembly 600 to achieve the speed adjustment of the motor assembly 300, a user can carry out one-handed operation, which greatly frees the user's other hand and enables the user to not have to put down the work on the hand to adjust the rotational speed in the process of manicure. And by pressing down the flexible top cover assembly 600 to achieve the start and stop of the motor assembly 300, which simplifies the operation process of the user adjusting the rotational speed during the process of manicure, and is convenient to use.

In this embodiment, the speed regulating assembly 500 can be a rotary press potentiometer, which is a variable resistor whose resistance value can be changed by rotating a knob of the potentiometer, and the rotary press potentiometer belongs to the prior art, and the specific adjustment principle is not be repeated.

In this embodiment, the motor assembly 300 includes a motor 320, a rotary shaft hinge 310 and a circuit board 400, one end of the rotary shaft hinge 310 is detachably connected to the polish head 200, and another end is connected to an output shaft of the motor 320, and the motor 320 is connected to the circuit board 400.

Figure 3:
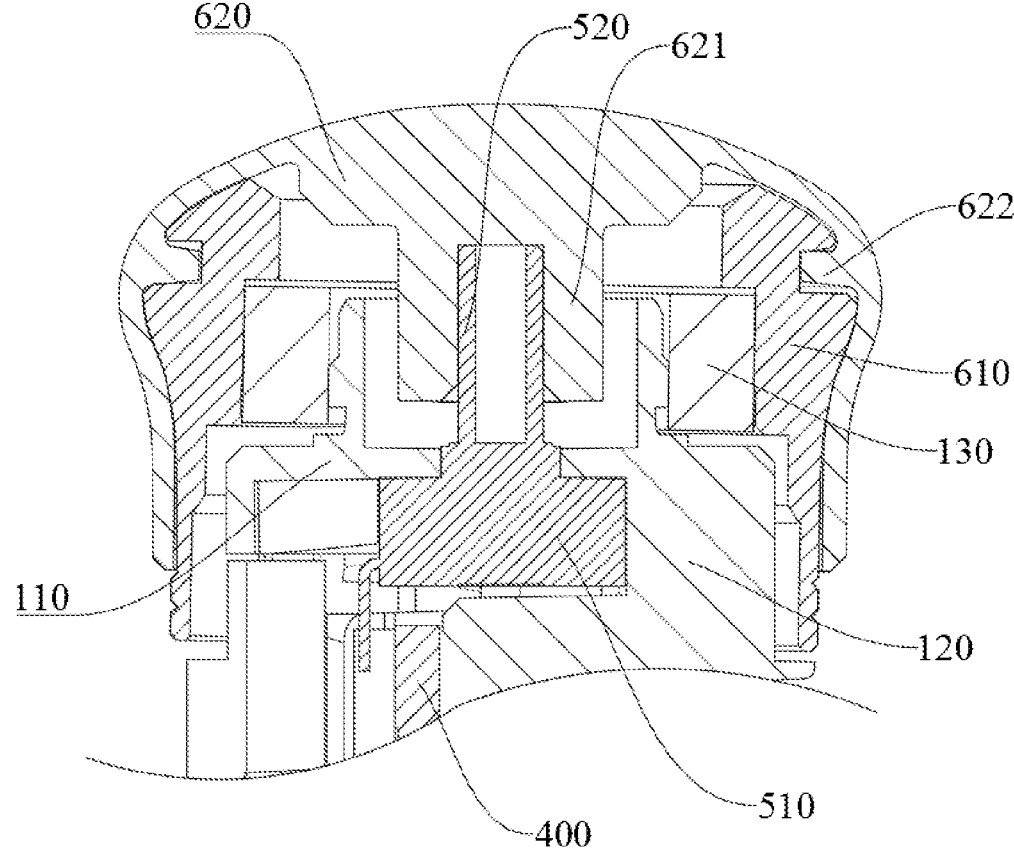
FIG. 3 is a schematic diagram of a structure of a shell assembly in the present disclosure; and, FIG. 4 is a schematic diagram of a structure of a flexible top cover assembly in the present disclosure.
Figure 4:
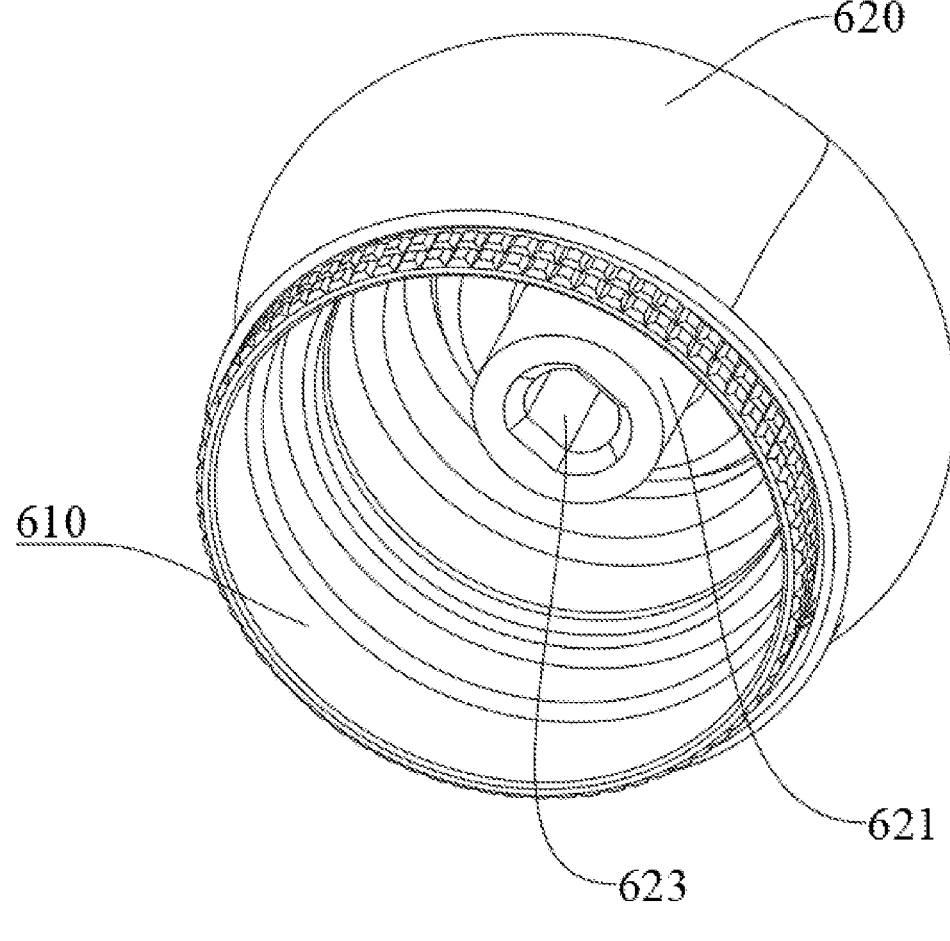

Referring to FIGS. 3 and 4, the flexible top cover assembly 600 includes a rotary sleeve 610 and a flexible top cover 620, one end of the rotary sleeve 610 is connected to one end of the shell assembly 100 away from the polish head 200, and another end is connected to the flexible top cover 620, and the flexible top cover 620 covers the speed regulating assembly 500.

In some embodiments, the rotary sleeve 610 is made of a hard material, such as a metal rotary sleeve 610. The rotary sleeve 610 has a lower friction with the shell assembly 100 to ensure that the rotary sleeve 610 rotates more smoothly relative to the shell assembly 100. The flexible top cover 620 is made of a soft elastic material, such as a silicone flexible top cover 620. The flexible top cover 620 of the soft material is able to ensure that an inner wall of the flexible top cover 620 has sufficient friction with the rotary sleeve 610 to avoid the flexible top cover 620 from rotating with respect to the rotary sleeve 610, and at the same time, can ensure that a side wall of the flexible top cover 620 has sufficient friction with the tabletop to facilitate the flexible top cover 620 rotating with respect to the tabletop. When the flexible top cover 620 is rotated, the rotary sleeve 610 drives the flexible top cover 620 to rotate, and the flexible top cover 620 drives the rotary shaft 520 to rotate.

By the combination of the rotary sleeve 610 and the flexible top cover 620, this embodiment ensures that the rotation between the rotary sleeve 610 and the shell assembly 100 is smoother, while at the same time ensures that the flexible top cover 620 has sufficient friction with the tabletop, achieving a simple structure.

In this embodiment, one end of the flexible top cover 620 away from the shell assembly 100 is provided with a connection portion 621, the connection portion 621 extends in a direction from the flexible top cover 620 towards the speed regulating assembly 500, and the connection portion 621 is connected to the speed regulating assembly.

In some embodiments, the rotary sleeve is sleeved on the shell assembly 100, and then the flexible top cover 620 is sleeved outside the rotary sleeve 610, while the connection portion 621 is sleeved on the rotary shaft 520 through a connection hole 623 to achieve a fixed connection between the flexible top cover 620 and the rotary shaft 520, so that the flexible top cover 620 is able to drive the rotary shaft 520 to rotate, and the rotary shaft 520 limits the flexible top cover 620, avoiding the flexible top cover 620 and the rotary sleeve 610 from falling off from the shell assembly 100. The rotary shaft 520 interacts with the flexible top cover 620, achieving a compact structure.

In this embodiment, one end of the connection portion 621 towards the polish head 200 is provided with a connection hole 623, a shape of the connection hole 623 is adapted to a shape of the rotary shaft 520, one end of the rotary shaft 520 away from the base 510 is provided inside the connection hole 623, and the connection hole 623 may be a waist-shaped hole.

In this embodiment, the flexible top cover 620 is one of a silicone flexible top cover 620 or a rubber flexible top cover 620. Silicone and rubber have good flexibility and elasticity to accommodate various surface conditions, and silicone and rubber have good abrasion resistance.

In this embodiment, an outer surface of the rotary sleeve 610 is provided with an annular groove, an inner surface of the flexible top cover 620 is provided with a ring protrusion 622, and the ring protrusion 622 is snapped into the annular groove.

In some embodiments, when assembling, the ring protrusion 622 of the flexible top cover 620 is first snapped into the groove to connect both the flexible top cover 620 and the rotary sleeve 610 together, and then both the flexible top cover 620 and the rotary sleeve 610 are sleeved on the shell assembly 100, which is easy to assemble. And by the cooperation of the ring protrusion 622 and the shell assembly 100, a friction between the flexible top cover 620 and the rotary sleeve 610 is enhanced.

In this embodiment, the shell assembly 100 includes a shell 150, a front shell 110, a back shell 120, a fixing cylinder 130, and a fixing ring 140. One end of the shell 150 is connected to the polish head 200 and another end of the shell 150 is connected to the flexible top cover assembly 600. The front shell 110 is arranged inside the shell 150. The back shell 120 is arranged inside the shell 150, and enclosed with the front shell 110 to form the mounting cavity. The fixing cylinder 130 is sleeved at both one end of the front shell 110 away from the polish head 200 and one end of the back shell 120 away from the polish head 200 for connecting the front shell 110 and the back shell 120 together. The fixing ring 140 is sleeved at both one end of the front shell 110 close to the polish head 200 and one end of the back shell 120 close to the polish head 200 for connecting the front shell 110 and the back shell 120 together.

In some embodiments, the front shell 110 and the back shell 120 are fastened together to enclose and form the mounting cavity. When assembling, firstly, the motor assembly 300, the circuit board 400, and the speed regulating assembly 500 are mounted into corresponding mounting positions of the back shell 120 in sequence, and then the front shell 110 is fastened to the back shell 120, then the fixing cylinder 130 is sleeved at both one end of the front shell 110 and one end of the back shell 120, and the fixing cylinder 130 hoops one end of the front shell 110 with one end of the back shell 120, then the front shell 110 and the back shell 120 are put into the shell 150, the fixing ring 140 is sleeved at both another end of the front shell 110 and another end of the back shell 120, the fixing ring 140 hoops both another end of the front shell 110 and another end of the back shell 120. By hooping the front shell 110 and the back shell 120 by the fixing ring 140 and the fixing cylinder 130, the assembly is convenient, and there is no need to punch holes for fixing the shell to avoid damage to the shell.

In this embodiment, one end of the front shell 110 away from the polish head 200 is provided with a first elastic protrusion, and one end of the back shell 120 away from the polish head 200 is provided with a second elastic protrusion, the first elastic protrusion and the second elastic protrusion both abut against an inner wall of the fixing cylinder 130, respectively. An outer wall of the fixing cylinder 130 is rotatably connected with the rotary sleeve 610.

In some embodiments, an inner wall of the fixing cylinder 130 is in contact with both an outer side plate of the front shell 110 and an outer side plate of the back shell 120. An outer wall of the fixing cylinder 130 is in contact with an inner wall of the rotary sleeve 610. The base 510 of the speed regulating assembly 500 is fixedly connected to both the front shell 110 and the back shell 120. The flexible top cover 620 is rotated to drive the rotary sleeve 610 to rotate with respect to the fixing cylinder 130, while the flexible top cover 620 drives the rotating shaft 520 to rotate with respect to the base 510. The first protrusion and the second protrusion both abut against the inner wall of the fixing cylinder 130, increasing both a friction between the fixing cylinder 130 and the front shell 110 and a friction between the fixing cylinder 130 and the back shell 120, making both a connection between the fixing cylinder 130 and the front shell 110 and a connection between the fixing cylinder 130 and the back shell 120 more stable.

In this embodiment, the nail drill for easy control further includes a display screen, the display screen is arranged on a side wall of the shell assembly 100, the display screen is electrically connected to the motor assembly 300 for displaying the rotational speed of the motor 320.

In some embodiments, the display screen is electrically connected to the motor assembly 300 to display the rotational speed of the motor assembly 300 in real time, which facilitates the user to quickly and precisely adjust to a desired speed, and is easy to use.

In this embodiment, the nail drill for easy control further includes a battery 700 and a charging connector. The battery 700 is arranged inside the mounting cavity and electrically connected to the motor 320 for supplying power to the motor assembly 300. An output end of the charging connector is arranged inside the mounting cavity, an output end of the charging connector is electrically connected to the battery 700, and an input end of the charging connector is arranged on a side wall of the shell assembly 100 for electrical connected to an external power source.

In some embodiments, when charging, the battery 700 is electrically connected to an external power supply through the charging connector to achieve the charging of the battery 700, so that there is no need to connect to an external power supply during the use of the nail drill, and it can be adapted to more usage scenarios.

In this embodiment, the nail drill for easy control further includes a power switch button 800, the power switch button 800 is arranged at the shell assembly 100, and the power switch button 800 is electrically connected to the circuit board 400 for controlling the connecting and disconnecting of the power supply. Turning off the power supply when the power supply is not required for use, avoids the danger of accidentally touching the flexible top cover 620 causing the motor assembly 300 to turn on.

In summary, the nail drill for easy control of the present embodiment includes a shell assembly 100, a polish head 200, a motor assembly 300, a speed regulating assembly 500, and a flexible top cover assembly 600. The speed regulating assembly 500 regulates the rotational speed of the motor assembly 300 and the start or stop of the motor assembly 300. The flexible top cover assembly 600 is rotatably provided at one end of the shell assembly 100 away from the polish head 200, and covers the speed regulating assembly 500. When using, holding the nail drill, tilting the flexible top cover assembly 600 of the nail drill to the desktop and sliding it, adjusting the rotational speed of the motor assembly 300, and regulating the rotational speed with one hand, greatly free the user's other hand, and enable the user not to have to put down the work of the hand to adjust the rotational speed in the process of manicuring. Pressing a top of the flexible top cover assembly 600, the motor assembly 300 stops; and pressing the top of the flexible top cover assembly 600 again, the motor assembly 300 rotates, achieving a pause function of the motor assembly 300. It can simplify the operation process of adjusting the rotational speed in the process of manicure and is convenient to use.

It is to be noted that the embodiments and the features in the embodiments in the present disclosure can be combined with each other without conflict.

It is to be noted that the present disclosure is described in terms of the specific structure and working principle of the present disclosure by taking the nail drill for easy control as an example, but the application of the present embodiment is not limited to the nail drill for easy control, and the application of the present disclosure can also be applied to the production and use of other similar workpieces.

It should be understood that the present disclosure is not limited to the precise structure already described above and illustrated in the accompanying drawings, and that various modifications and changes can be made without departing from its scope. The scope of the present disclosure is limited only by the appended claims.

The above mentioned are only the better embodiments of the present disclosure, and are not intended to limit the present disclosure. Any modifications, equivalent substitutions, improvements, etc. made within the spirits and principles of the present disclosure are included in the protection scope of the present disclosure.

What is claimed is:

1. A nail drill for easy control comprising:
a shell assembly having a mounting cavity inside the shell assembly;
a motor assembly, provided inside the mounting cavity;
a circuit board electrically connected to the motor assembly and provided inside the mounting cavity;
a polish head provided at a distal end of the shell assembly, wherein the polish head is connected to an output end of the motor assembly;
a speed regulating assembly including a base and a rotary shaft protruding proximally from the base, where the speed regulating assembly is provided at a proximal end of the shell assembly and is electrically connected to the motor assembly via the circuit board; and
a flexible top cover assembly, rotatably provided at the proximal end of the shell assembly where the speed regulating assembly is disposed within an interior space of the flexible top cover assembly defined by inner walls of the rotary sleeve and flexible top cover;
wherein the flexible top cover assembly comprises a rotary sleeve and a flexible top cover, one end of the rotary sleeve is connected to one end of the shell assembly away from the polish head, and another end of the rotary sleeve is connected to the flexible top cover, and the flexible top cover has a connection portion coupled to the rotary shaft of the speed regulating assembly;
wherein when the flexible top cover is rotated, the flexible top cover drives the rotary shaft to rotate and a rotational speed of the motor assembly is adjusted via interaction between the base and the circuit board, and when the flexible top cover is pressed, the rotary shaft is pressed and a start or a stop of the motor assembly is controlled through interaction between the base and the circuit board.

2. The nail drill for easy control according to claim 1, wherein the connection portion is provided at one end of the flexible top cover away from the shell assembly, and the connection portion extends in a direction from the flexible top cover towards the speed regulating assembly.

3. The nail drill for easy control according to claim 1, wherein the flexible top cover is a silicone flexible top cover or a rubber flexible top cover.

4. The nail drill for easy control according to claim 1, wherein an annular groove is provided at an outer surface of the rotary sleeve, a ring protrusion is provided at an inner surface of the flexible top cover, and the ring protrusion is snapped into the annular groove.

5. The nail drill for easy control according to claim 4, wherein the shell assembly comprises:
a shell, wherein one end of the shell is connected to the polish head, and another end of the shell is connected to the flexible top cover assembly;
a front shell, provided inside the shell;
a back shell, provided inside the shell, wherein the back shell and the front shell are enclosed to form the mounting cavity;
a fixing cylinder, sleeved at both one end of the front shell away from the polish head and one end of the back shell away from the polish head, for fixedly connecting the front shell and the back shell together; and
a fixing ring, sleeved at both one end of the front shell close to the polish head and one end of the back shell close to the polish head, for fixedly connecting the front shell and the back shell together.

6. The nail drill for easy control according to claim 5, wherein the front shell is provided with a first elastic protrusion at one end of the front shell away from the polish head, the back shell is provided with a second elastic protrusion at one end of the back shell away from the polish head, the first elastic protrusion and the second elastic protrusion respectively abuts against an inner wall of the fixing cylinder, and an outer wall of the fixing cylinder is rotatably connected with the rotary sleeve.

7. The nail drill for easy control according to claim 1, further comprising a display, the display is provided at a side wall of the shell assembly, the display is electrically connected to the motor assembly for displaying a rotational speed of a motor.

8. The nail drill for easy control according to claim 1, wherein the nail drill for easy control further comprises: a battery, provided inside the mounting cavity, and electrically connected to the motor assembly for powering the motor assembly; and a charging connector, provided inside the mounting cavity, wherein an output end of the charging connector is electrically connected to the battery, and an input end of the charging connector is provided on a side wall of the shell assembly for electrically connecting to an external power source.

9. The nail drill for easy control according to claim 1, wherein the nail drill for easy control further comprises a power switch button, the power switch button is provided at the shell assembly, and the power switch button is electrically connected to the motor assembly for controlling a connection and a disconnection of a power supply.

* * * * *